United States Patent [19]

Clyburn

[11] Patent Number: 4,628,919

[45] Date of Patent: Dec. 16, 1986

[54] DYNAMIC EXTERNAL FIXATOR AND METHOD OF USE

[76] Inventor: Terry A. Clyburn, 4006 Sue Ellen, Houston, Tex. 77087

[21] Appl. No.: 530,608

[22] Filed: Sep. 9, 1983

[51] Int. Cl.$^4$ ................................................ A61F 5/04
[52] U.S. Cl. .................................. 128/92 ZK; 128/92; 128/92 ZZ
[58] Field of Search ................. 128/92 A, 92 R, 84 B, 128/88

[56] References Cited

U.S. PATENT DOCUMENTS

| | | | |
|---|---|---|---|
| 4,312,336 | 1/1982 | Danieletto et al. | 128/92 A |
| 4,548,199 | 9/1985 | Agee | 128/92 A |
| 4,554,915 | 11/1985 | Brumfield | 128/92 A |

Primary Examiner—Robert Peshock
Assistant Examiner—C. W. Shedd
Attorney, Agent, or Firm—Sherman and Shalloway

[57] ABSTRACT

A dynamic external fixator is disclosed which is designed to be applied externally along side the wrist by way of elongated bone fixation pins. The fixator includes two elongated legs connected by a universal joint. The proximal leg includes a series of holes for receipt of the bone fixation pins and associated threaded retainers to retain the bone fixation pins in the desired orientations. The distal leg includes a pistoning device which allows adjustability of the length thereof and further includes at least one set screw which reciprocates in a slot formed in the leg to enable the adjustment of the extension of the pistoning device thereof. The distal leg further includes a series of holes which receive the elongated bone fixation pins and further includes threaded members usable to maintain the bone fixation pins in a desired orientation. The universal joint includes means associated therewith which enables adjustment of the degree of movement of the proximal leg with respect to the distal leg and may also include means for indicating the degree of range of movement allowed in various adjusted positions thereof.

20 Claims, 6 Drawing Figures

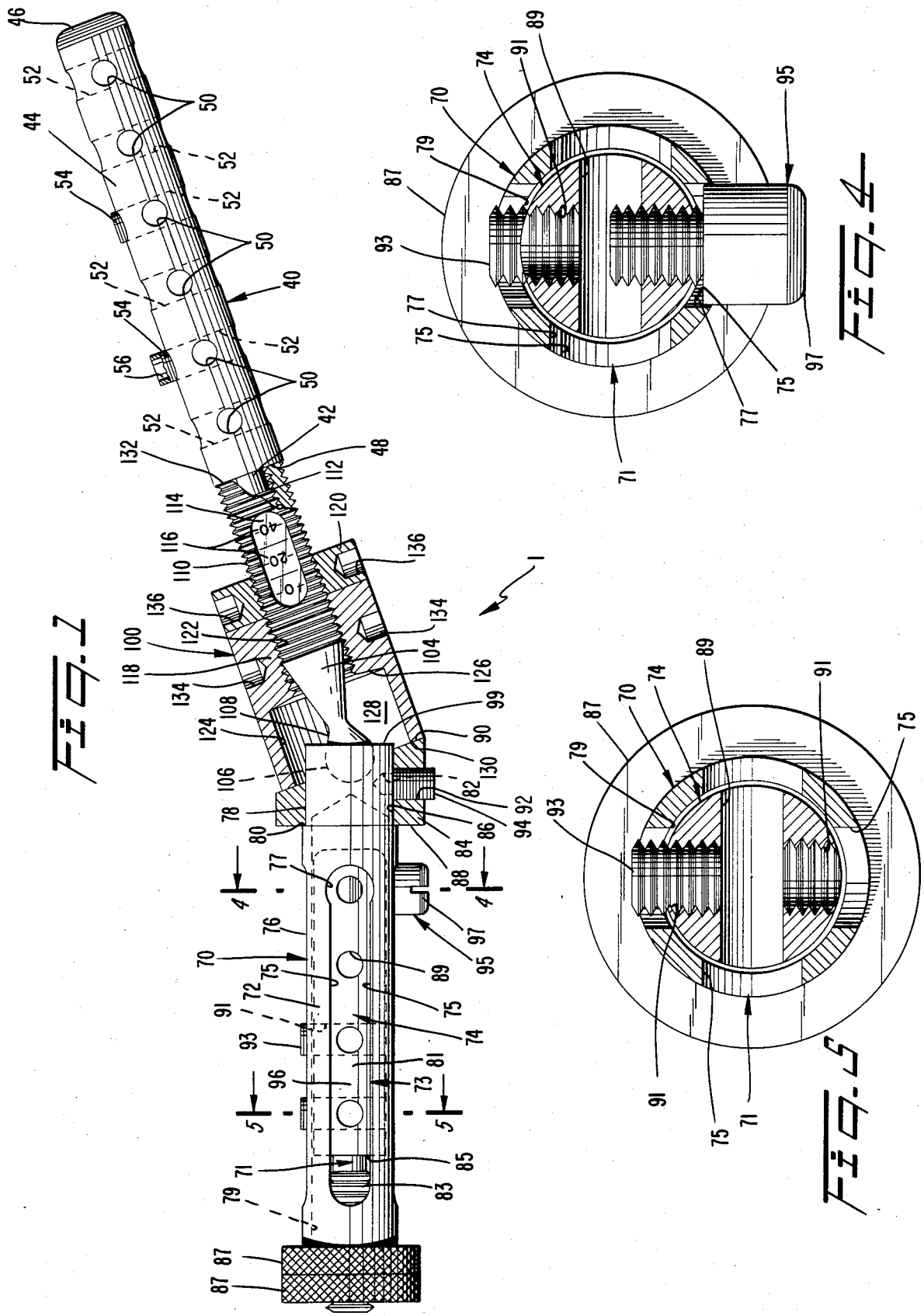

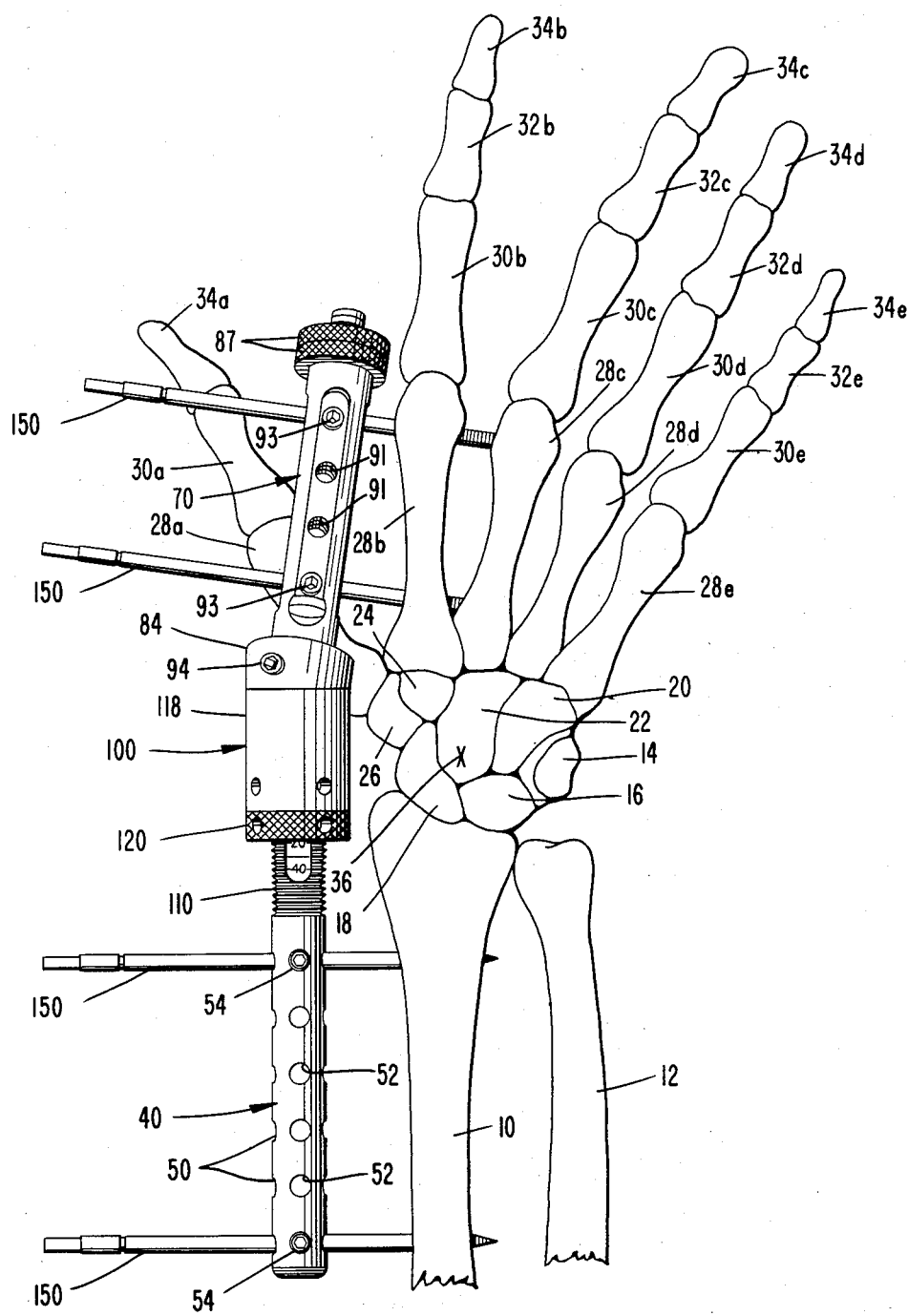

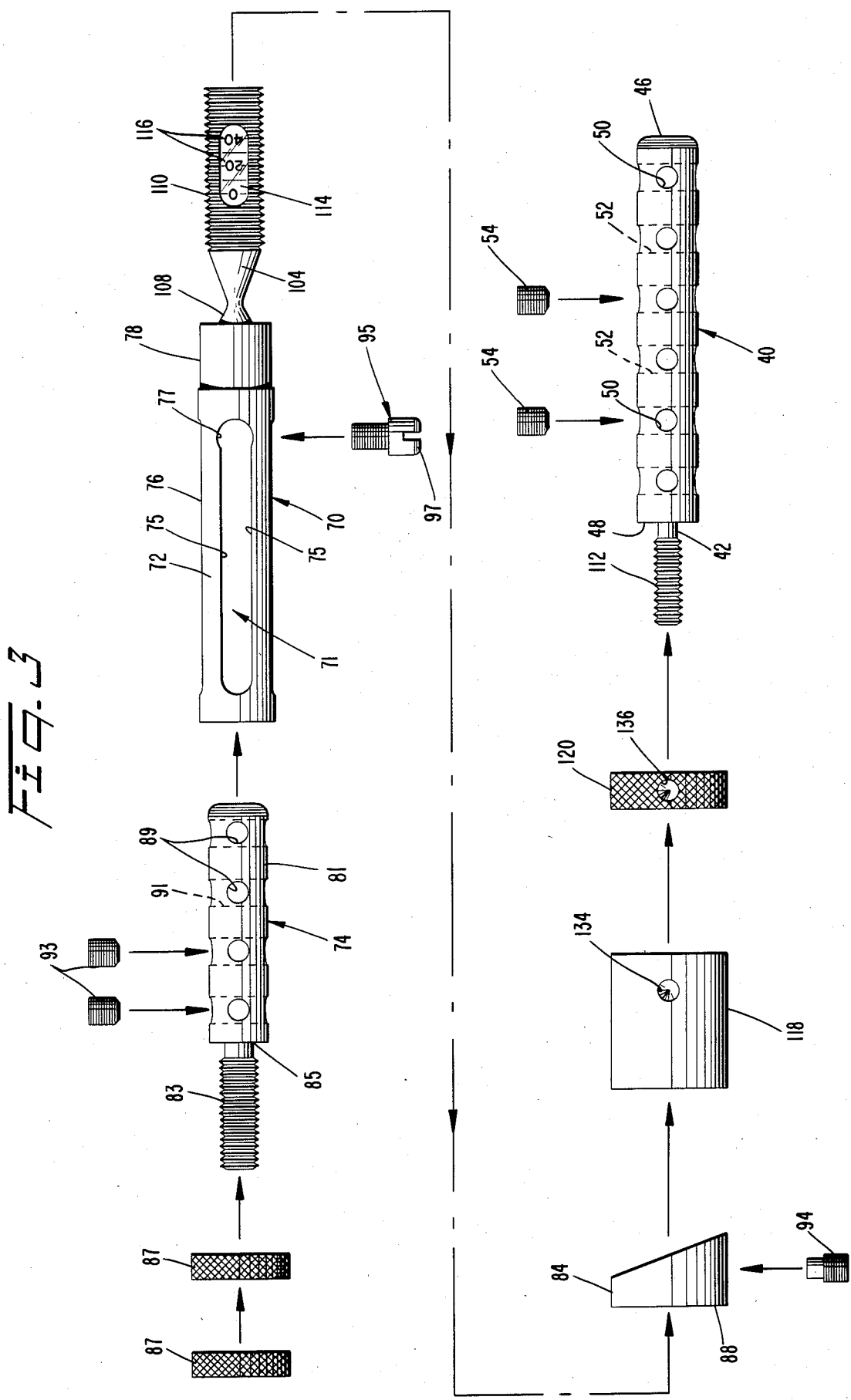

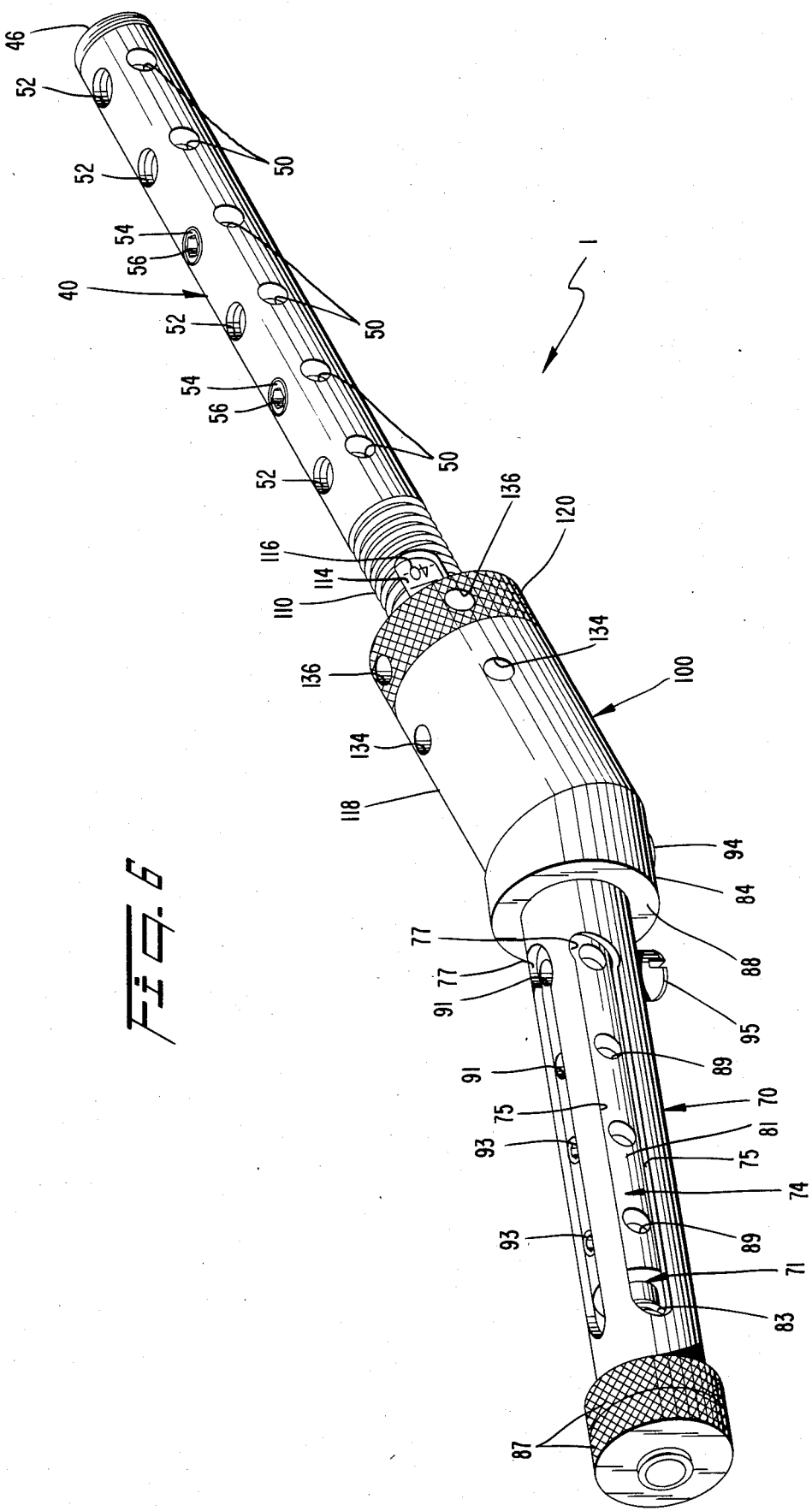

DYNAMIC EXTERNAL FIXATOR AND METHOD OF USE

BACKGROUND OF THE INVENTION

This invention relates to a dynamic external fixator usable to aid in the treatment of bone fractures in the region of the human wrist. It is well known that closed cast immobilization is inadequate for the treatment of displaced fractures of the distal radius in which loss of length of the involved bones is a significant risk. This loss of length as well as loss of normal radial and volar tilt are directly correlated with insufficient and inferior treatment techniques. Loss of range of motion of the wrist joint due to inferior treatment techniques poses a serious problem.

As noted by Lidstrom in his article entitled "Fractures of the Distal End of the Radius: A Clinical and Statistical Study of End Results", concern with residual stiffness following closed methods of treatment is found in the works of multiple authors of the late 19th and 20th centuries. They advocated early range of motion without immobilization, thus recognizing the need for early motion, but failed to recognize the importance of maintenance of reduction. As further noted therein, a long term studies with large numbers of patients have a shown a direct correlation of functional results to the adequacy and maintenance of reduction as well as to the severity of the original fracture. In the series reported by Lidstrom, fractures of the displaced, comminuted type treated by closed methods resulted in an 81% incidence of significant loss of motion. Therein, the results were also related to the types of fracture found and in situations where the fractures were of the displaced, comminuted type the results were either poor or fair in 56% of the cases.

It has also been recognized in the art that it is desirable for the wrist to have a certain degree of mobility during the treatment of wrist fractures. The prior art has advocated the use of a functional splint in order to maintain length and reduction while allowing motion, however, significant loss of volar tilt and collapse have been seen with both displaced extra-articular and intra-articular fractures.

The use of skeletal external fixation, generally speaking, is known and has been quite successful in maintaining length, volar and radial tilt and thus improving functional results in the healing of fractures. In the prior art, numerous modes are disclosed utilizing the combination of skeletal pin fixation and plaster. The use of the combination of plaster and skeletal pin fixation is not without its complications. D. P. Green in his paper "Comminuted Fractures of the Distal End of the Radius" notes that in a comprehensive series, 50% of the patients had loss of pronation-supination and only 15% of the patients had normal wrist motion at long term follow up. The most significant problem involved in the procedure involved pin care beneath the plaster and Green notes a 33% incidence of pin cite drainage problems.

The introduction of external skeletal fixation marked a significant advantage in the treatment of comminuted, displaced fractures of the distal radius. The principle employed in this procedure is that of longitudinal traction applied to the skeleton by proximal and distal pins. Maintenance of the device is necessary until healing is adequate to assure maintenance of reduction. Unfortunately, in the prior art, the system does not allow motion at the wrist during the period of fracture immobilization.

While the above described treatment is much improved over previous methods, significant problems result due to the prolonged immobilization of the wrist which is necessary during the treatment. W. P. Cooney, et al. in their paper "External Pin Fixation For Unstable Colles' Fractures" report on their review of 60 patients 2 years after a fracture of the wrist. Their review indicates that the range of motion of the wrist is decreased in most cases in all planes about the wrist. Thus while this method does maintain length and radial and volar tilt which are known to improve functional results, however, immobilization of the wrist during the healing process may result in prolonged recovery of motion or, as shown by Cooney, et al., residual loss of motion as late as two years post injury.

The following U.S. Patents are known to applicant: U.S. Pat. No. 1,789,060 to Weisenbach, U.S. Pat. No. 435,850 to Siebrandt U.S. Pat. No. 2,439,995 to Thrailkill, U.S. Pat. No. 3,941,123 to Volkov, et al. and U.S. Pat. No. 4,312,336 to Danieletto, et al. While these patents appear to be directed to external fixators of various types, the present invention is believed to be patentably distinct therefrom as teaching the combination of fixation of the wrist joint fracture while allowing freedom of movement of the joint itself, with the further provision of adjustability of the freedom of movement. These and other differences will become apparent from a reading of the specific description of the preferred embodiment hereinafter.

SUMMARY OF THE INVENTION

The present invention overcomes the problems inherent in prior art devices by providing a dynamic external fixator including the following features:

(1) A proximal leg portion including a plurality of holes which receive elongated bone fixation pins and a corresponding plurality of threaded holes associated with the first mentioned holes which receive threaded pin retention members.

(2) A distal leg portion also including a plurality of holes which receive elongated bone fixation pins, also including further threaded holes associated with first mentioned holes which receive threaded members which retain in position the pins, and the above mentioned holes being mounted on a member comprising a piston slidably mounted in a cylinder portion of the distal leg. Retention members are provided at both ends of the piston member so as to enable its retention with respect to the cylinder portion in one or more relative positions thereof.

(3) The proximal and distal legs are connected together through a ball and socket joint. Means are provided associated with this ball and socket joint for enabling adjustability of the freedom of motion between the proximal and distal legs. The adjustment device may further include means for indicating the degree of freedom of movement to which the ball and socket joint has been adjusted.

Also disclosed herein are the various methods of using the apparatus of the present invention in conjunction with the healing of a fractured joint, preferably the wrist. These methods will be described in great detail hereinafter.

Accordingly it a first object of the present invention to provide a dynamic external fixator usable to aid in the healing of a fractured bone preferably within the region of the human wrist.

It is a further object of the present invention to provide a dynamic external fixator which includes a high degree of adjustability for the desired positions of elongated bone fixation pins usable therewith.

It is a further object of the present invention to provide a dynamic external fixator including means for retaining such elongated bone fixation pins in a desired configuration with respect to leg portions thereof.

It is a yet further object of the present invention to provide a dynamic external fixator including at least one leg which includes a pistoning means which allows extensibility thereof.

It is a yet further object of the present invention to provide a dynamic external fixator including two leg portions connected together by a ball and socket joint.

It is a still further object of the present invention to provide a dynamic external fixator wherein the range of motion of the ball and socket joint thereof may be adjustable.

It is a yet further object of the present invention to provide a dynamic external fixator which not only includes a means to adjust the range of motion of the ball and socket joint thereof but further includes means indicating the degree of range of motion to which the ball and socket joint thereof has been adjusted.

It is a still further object of the present invention to provide methods of utilization of the dynamic external fixator which methods enable one skilled in the art to facilitate the healing of a fractured bone preferably in the region of the wrist joint.

It is a yet further object of the present invention to provide such methods which in conjunction with the dynamic external fixator facilitate the healing while allowing a predetermined freedom of movement of the joint which may be adjustable through practicing of the method within predetermined limits.

These and other objects and aspects of the present invention may be better understood through the following description of the preferred embodiments of the invention when taken in conjunction with the accompanying drawings.

BRIEF DESCRIPTION OF THE DRAWINGS

FIG. 1 shows a side view of a dynamic external fixator according to the present invention.

FIG. 2 shows a top view of the distal portions of the radius and ulna of an arm in conjunction with the bones of the wrist and hand thereof, with the apparatus of the present invention fastened thereto.

FIG. 3 shows an exploded view of the dynamic external fixator of the present invention.

FIG. 4 shows a cross-sectional view along the line 4—4 of FIG. 1.

FIG. 5 shows a cross-sectional view along the line 5—5 of FIG. 1.

FIG. 6 shows a perspective view of the dynamic external fixator of the present invention.

DESCRIPTION OF THE PREFERRED EMBODIMENTS

Referring to FIG. 2, the dynamic external fixator is shown as attached to the bones of the hand and lower arm of a human skeleton. As is well known, the bones of the lower arm consist of the radius 10 and the ulna 12. The wrist consists of the triangular bone 14, the lunate bone 16, the scaphoid bone 18, the hamate bone 20, the capitate bone 22, the trapezoid bone 24, and the trapezium bone 26. The hand consists of the metacarpal bones 28a-e, the proximal flanges 30a-e, the middle flanges 32b-e and the distal flanges 34a-e. Studies have shown that the center of rotation of the bones of the wrist is approximately at the spot referred to by reference numeral 36.

Referring now to FIGS. 1-6, the dynamic external fixator 1 of the present invention is seen to include a proximal leg portion 40, a distal leg portion 70 and an intermediate hinge member 100.

The intermediate hinge member 100 includes a cylindrical portion 110, a conical tapering portion 104 extending from one end of the cylindrical portion 102 and a ball portion 106 extending from the end of the tapered portion of smallest size. If desired, the tapered portion 104 may merge with the ball portion 106 through a tapered portion 108. The cylindrical portion 110 has peripheral threads throughout its length and also includes a bore 112 which is threaded as well. The cylindrical portion 110 further includes a flat surface 114 of elongated dimension machined into the surface thereof and this surface 114 includes indicia 116 written thereon for a purpose to be described hereinafter. As shown in the drawings, a cylindrical cup shaped sleeve 118 is threaded over the cylindrical portion 110 of the hinge portion 100 and a lock nut 120 is threaded over the cylindrical portion 110 behind the cup shaped sleeve 118 and is provided to enable the locking of the position of the cup shaped sleeve 118 in predetermined desired positions thereof. The cup shaped sleeve 118 includes a first small bore 122 including threads complimentary to the threads on the cylindrical portion 110, a large bore 124 and a substantially conical shoulder 126 which connects the bores 122 and 124. The bore 124 and the shoulder 126 define a chamber 128 which, in assembly, encompasses the ball 106 and associated socket thereof. The cup shaped sleeve 118 terminates at its distal end at a flat surface 130 for a purpose to be described hereinafter.

As stated above, the proximal leg 40 is threaded into the bore 112 of the cylindrical portion 110 of the hinge portion 100. For this purpose, the proximal leg portion 40 has a reduced diameter shaft 42 which includes external threads thereon complimentary to the internal threads in the bore 112 to thereby enable the threading of this shaft therein. The proximal leg portion further includes a larger diameter substantially cylindrical portion 44 which includes a closed end portion 46, a shoulder 48 defining the intersection between the portions 42 and 44, which shoulder abuts a shoulder 132 at the proximal end of the hinge portion 100. The portion 44 of the proximal leg portion 40 includes a number of holes drilled therethrough. A first set of holes 50 have smooth bores therein while a second set of holes 52 arranged substantially perpendicularly to the holes 50 and each of which intersects a hole 50 has internal threads therein which receive set screws 54. In use, elongated bone fixation pins 150 are inserted into the holes 50 and are retained in a particular desired orientation by the set screws 54 which are threaded into the holes 52 so as to frictionally bear against a side portion of the elongated bone fixation pins. The proximal leg portion 40 provides more holes 50 and 52 than are necessary for the required number of pins in a particular procedure, and this is the case so as to provide several different locations for each pin and thus provides flexibility in the invention. It is noted at this point that the cup shaped sleeve 118 may have bored therein a series of circumferentially spaced holes 134 which are adapted to receive a tool (not shown) which is provided so as to rotate the sleeve 118. Similarly the lock nut 120 may include holes 136 for the same purpose. Further it is noted that the threaded members 54 may include Allen type heads including a hexagonal recess 56 adapted to receive a tool with a hexagonal periphery for the purpose of turning the threaded member.

The distal leg portion 70 includes two relatively slidable members, namely, a cylinder portion 72 and a piston portion 74. The cylinder portion 72 includes a large diameter substantially cylindrical portion 76, a smaller diameter portion 78 and a shoulder 80 connecting the two portions 76 and 78. The smaller diameter portion 78 includes a radial bore 82 extending slightly into the surface thereof for a purpose to be described hereinbelow. As shown in the drawings, a compound angle sleeve 84 including an internal diameter bore 86 adapted for a slidable fit over the portion 78 is slidably mounted over the portion 78 and has an end 88 which abuts the shoulder 80 of the cylindrical portion 72. The end 88 comprises a face which is substantially perpendicular to the cylindrical extent of the outer periphery of the compound angle sleeve 84. At the other end of the compound sleeve 84, a flat face 90 is provided which is cut at an acute angle to the other face 88 as shown in the drawings. The sleeve 84 includes a threaded hole 92 through which is threaded a lock nut 94 the end of which extends into the recess bore 82 of the portion 78 to thereby fixedly lock the compound angle sleeve 84 onto the portion 78 in assembly. The larger diameter portion 76 of the cylinder portion 72 includes a chamber 96 formed therein including an outer periphery adapted to slidably receive the piston member 74. As shown in the drawings, in the preferred embodiment, the portion 76 includes four elongated openings 71 formed there through. The openings include an elongated portion 73 formed by parallel sides 75 and at one end thereof a substantially circular portion 77 attached at one end to the parallel sides 75. The circular portion 77 is provided for a purpose to be described hereinafter. At its distal end, the portion 76 includes an opening 79 of the same outer dimension as the chamber therein and sized to slidably receive the piston 74.

As further shown in the drawings, the piston 74 includes a head portion 81, a reduced size threaded portion 83 and a shoulder 85 interconnecting the portions 81 and 83. The threaded portion 83 extends out the opening 79 of the cylinder portion 72 and as shown has threaded thereon a pair of distraction nuts 87 which enable the locking of the position of the piston member 74 so as to define its inwardmost position within the chamber 71. The piston 74 further includes a series of holes 89 extending there through which are sized to receive elongated bone fixation pins and further threaded bores 91 which extends substantially perpendicularly to the bore 89, intersect the bores 89 and receive threadedly set screws 93 which are adapted to engage frictionally the elongated bone fixation pins so as to retain them in desired orientations thereof. As shown, a large headed locking screw 95 including a head portion 97 with an outer periphery corresponding to the portion 77 of the elongated slot 73 may be provided. This screw 95 may be threaded into one of the holes 91 in the piston member 74 with the outer periphery of the head 97 thereof extending within the portion 77 to thereby lock the movement of the piston 74 with respect to the cylinder 72. The underside of head 97 may also overlay the elongated portion 73 to thereby frictionally retain the piston in a desired position. The reduced diameter portion 78 of the cylinder 72 includes socket 99 which envelopes the ball 106 of the hinge portion 100 and enables respective universal movement therebetween. As shown in FIG. 1, with the face 130 of the sleeve 118 bearing against the face 90 of the compound angle sleeve 84, it is seen that the position of the ball 106 with respect to the socket 99 is rigidly fixed and no relative movement of the ball 106 with respect to the socket 99 is possible. As the sleeve 118 is backed away from the compound sleeve 84 through threading in the proximal direction of both the lock nut 120 and the sleeve 118, it is seen that the range of motion of the ball 106 and thereby the proximal leg 40 with respect to the socket 99 and thereby the distal leg 70 increases progressively as the sleeve 118 is progressively unthreaded in the proximal direction. At some point after the sleeve 118 has been threaded a sufficient distance in the proximal direction, the ball 106 and socket 99 will exhibit range of motion therebetween unlimited by the sleeve 118. Thus, it is seen, that the lock nut 120 may be used to retain the cylindrical sleeve 118 in a position somewhere between the most restricted and least restricted configurations thereof to thereby provided infinite adjustability of the range of motion of the ball 106 and socket 99. The surface 114 and indicia 116 are provided so as to enable precise adjustment of the position of the sleeve 118 with respect to the compound angle sleeve 84, and the indicia 116 comprise numerals or letters or other indicia indicative of the amount of range of motion being provided in a particular position with the proximal face of the lock nut 120 providing the means to indicate which numeral or other indicia 116 the position of the sleeve 118 corresponds to.

Now the preferred embodiment of the dynamic external fixator 1 having been described, the preferred methods of utilizing the fixator one will now be described.

The dynamic external fixator as disclosed hereinabove is designed for use, mainly, in treating a type of bone fracture known as the "Colles fracture." This fracture is located at the distal end of the radius bone of the arm and more particularly is located in the region of the joint between the radius bone and the wrist. In fractures of this type, fragments of bone are commonly found in the joint, not loose but rather within the joint tissues. The dynamic external fixator of the present invention when properly installed keeps the joint in distraction by separating the adjacent bones and tightening the ligaments surrounding these bones.

When the arm and hand are naturally hanging at the side of a person, the normal hand may be described with respect to the lower arm as in slight flexion toward the body and as exhibiting slight ulnar deviation in the direction of the ulna. The dynamic external fixator of the present invention is specifically designed to duplicate this natural position of the hand with respect to the arm when mounted in place on the lower arm and hand through the use of elongated bone fixation pins. For the best results, the center of rotation of the ball 106 is preferably aligned with the center of rotation 36 of the wrist in one plane, namely the frontal or coronal plane. The dynamic external fixator only restrains the rotation of the wrist in this one plane, however, this restraint is sufficient to promote the healing processes of the fracture. The pistoning action of the piston 74 with respect to the cylinder 72 allows for a small amount of ulnar deviation in situations wherein the piston 74 is not locked in position with respect to the cylinder 72. If such ulnar deviation is not desired, the piston 74 is locked in position with respect to cylinder 72 through the use of the lock nut 87 and screw 95, the operation of which have been disclosed above.

In utilizing the dynamic external fixator of the present invention, the following steps are followed:

(1) The proper anesthetic is utilized which may under the discretion of the physician be local or general.

(2) A small incision is made either adjacent the radius or adjacent the metacarpal bone through which the first hole is to be drilled. If desired, this first hole may be made in a free hand fashion. There are a number of ways of making a threaded hole in a bone, the most common of which comprise either drilling the hole with a self tapping thread or conversely first drilling a pilot hole and subsequently threading the pilot hole with a self tapping thread. Either approach will result in satisfactory holes for the purposes of the practicing of this invention. After the first hole is drilled whether in the metacarpal bone or the radius the subsequent holes necessary for placement of the bone fixation pins must be drilled using a drill guide of one sort or another. A drill guide is necessary for the subsequent holes so as to drill the holes in appropriate positions so as to line up with the pin holes 50, 89 in the dynamic external fixator. The drill guide may be a separate device including holes at the proper spacing or, if desired, the dynamic external fixator itself may be used as the guide with the appropriate drill bits being placed through the holes 50, 89 on their way to the respective bones.

(3) After the appropriate holes have been drilled and threaded by whichever method is used, the elongated bone fixation pins 150 are then threaded into the respective holes. The other ends of the elongated bone fixation pins 150 are then inserted through the holes 50, 89 of the dynamic external fixator and are retained in their appropriate positions by respective locking screws 54, 93.

(4) When the dynamic external fixator 1 is initially installed as described above, the sleeve 118 face 130 is threaded into engagement with the face 90 of the compound angle sleeve 84 so that the ball 106 is restrained from movement in the socket 99. As such, the proximal leg 40 is prevented from pivoting through the ball 106 with respect to the distal leg 70. With the ball locked in this fashion, if the piston 74 is not locked with respect to the cylinder 72, the above described ulnar deviation of the hand with respect to the wrist is possible. If the piston is on the other hand locked, such ulnar deviation is prevented.

(5) As the Colles fracture gradually heals, the sleeve 118 may be gradually threaded away from the compound angle sleeve 84 so as to allow increasing amounts of freedom of movement of the wrist. The flat portion 114 and indicia 116 of the cylindrical portion 110 of the hinge 100 provide an indication of the degree of freedom of movement arrived at by the particular orientation of the sleeve 118 with respect to the sleeve 84. In the preferred embodiment, every rotation of the sleeve 118 results in an additional approximately 10 degrees of freedom of movement of the joint. This figure should be considered to be merely exemplary and the pitch of the threads on the cylindrical portion 110 may be made at any desired amount with the inner bore 122 of the sleeve 118 being correspondingly threaded so as to provide any desired amount of change in freedom of movement per rotation of sleeve 118.

(6) It should be expected that body fluids will drain from the skin openings where the elongated bone fixation pins enter the body. In this regard, the elongated bone fixation pins are carefully sterilized before such insertion and after such insertion are covered with sterilized dressings which are periodically changed so as to remove the fluids therefrom. It is anticipated that the treatment of the fracture utilizing the dynamic external fixator of the present invention may extend over a period of eight to ten weeks, however, this period of time will vary from patient to patient based upon (a) severity of the fracture, (b) the speed with which a particular patient heals, and (c) other complications which may arise during the treatment.

While the invention has been described above with respect to a specific embodiment thereof and method as to its practice, it should be clear that various modifications and alterations can be made within the scope of the invention without departing therefrom. It is intended that the invention described hereinabove only be limited by the following claims.

I claim:

1. A dynamic external fixator comprising:
   (a) a proximal leg portion including first means for retaining at least one bone fixation pin therein;
   (b) a distal leg portion including second means for retaining at least one bone fixation pin therein said distal leg portion including adjusting means for allowing controllable elongation and contraction thereof, said second means forming a part of said adjusting means, said adjusting means comprising a cylinder and a piston slidably mounted in said cylinder, said piston including limit stop means for constraining motion of said piston with respect to said cylinder within predetermined limits;
   (c) universal joint means connecting said proximal leg portion to said distal leg portion and facilitating substantially universal movement therebetween; and
   (d) selectively positionable control means cooperating with said universal joint means, during a period of patent treatment, for selectively restricting the range of motion through which said universal joint means is free to move, said control means being infinitely adjustable from a position permitting unrestrained movement of said universal joint means to another position which substantially prevents movement of said universal joint means and thereby adjustably controlling the freedom of motion of said proximal leg portion with respect to said distal leg portion.

2. The invention of claim 1, wherein said first means comprises a first hole for receiving therethrough a bone fixation pin, and a second hole intersecting said first hole and threadably receiving a locking screw which frictionally engages said bone fixation pin to thereby retain said bone fixation pin in a predetermined orientation.

3. The invention of claim 2, wherein said first means comprises a plurality of said first hole, said second hole and said locking screw.

4. The invention of claim 2, wherein said second means comprises a third hole for receiving therethrough a further bone fixation pin, and a fourth hole intersecting said third hole and threadably receiving a further locking screw which frictionally engages said further bone fixation pin to thereby retain said further bone fixation pin in a predetermined orientation.

5. The invention of claim 1, wherein said proximal leg portion is removably connected to said universal joint means and said first means comprises at least four bone fixation pin receiving holes.

6. The invention of claim 1, wherein said universal joint means comprises a ball and socket joint.

7. The invention of claim 6, wherein said socket comprises an integral portion of said distal leg portion.

8. The invention of claim 1, wherein said selectively positionable control means comprises:
 (a) a first sleeve fixedly mounted on one of said proximal or distal leg portions;
 (b) a second sleeve adjustably mounted on said universal joint means; and
 (c) said first sleeve including a first face facing a second face on said second sleeve, whereby, when said first face abuts said second face, said universal joint means is substantially frozen in a fixed position and when said second sleeve is moved away from said first sleeve to thereby define a spacing between said first face and said second face, said universal joint means allows movement between said proximal and distal leg portions to an extent defined by said spacing.

9. The invention of claim 8, wherein said first sleeve has a longitudinal axis coinciding with a longitudinal axis of said one of said proximal or distal leg portions, said first face comprising a flat face in a plane at an obtuse angle to said longitudinal axis of said one of said proximal or distal leg portions, the other of said proximal or distal leg portions being connected to said universal joint means and having a longitudinal axis aligned with said first sleeve longitudinal axis, whereby when said first face abuts said second face, said proximal leg portion is oriented at an obtuse angle to said distal leg portion.

10. The invention of claim 8, wherein said universal joint means includes indicating means for indicating the amount of said movement between said proximal and distal leg portions.

11. A method of treating a Colles fracture of the distal radius of an arm comprising the steps of:
 (a) forming at least one hole in the radius of said arm and at least one hole in a bone of an associated hand distal of a wrist attached to said arm:
 (b) fixedly placing a bone fixation pin first end in each said hole;
 (c) fixedly attaching a second end of all the bone fixation pins associated with said radius to a proximal leg of a dynamic external fixator;
 (d) fixedly attaching a second end of all the bone fixation pins associated with said hand bone to a distal leg of said dynamic external fixator;
 (e) said pins so orienting said dynamic external fixator as to align a universal joint thereof with the center of rotation of the associated wrist in one plane thereof;
 (f) initially constraining said proximal and distal legs from relative movement via constraint of said universal joint; and
 (g) gradually allowing increasing freedom of movement of said universal joint through gradual controlled release of said constraint of said universal joint to thereby allow increasing freedom of movement of said arm with respect to said hand to thereby heal said Colles fracture while retaining maximum freedom of movememt of said wrist.

12. The method of claim 11, further including, prior to said first mentioned fixedly attaching step, the step of reciprocating said proximal leg with respect to said universal joint to align said proximal leg with said radius hole.

13. A dynamic external fixator comprising:
 (a) a proximal leg portion including first means for retaining at least one bone fixation pin therein;
 (b) a distal leg portion including second means for retaining at least one bone fixation pin therein;
 (c) joint means connecting said proximal leg portion to said distal leg portion and facilitating angular movement therebetween; and
 (d) means associated with said joint means and adjustable longitudinally along said proximal leg portion for adjustably controlling the extent of motion of said joint means to an indicated extent and thereby adjustably controlling the freedom of motion of said proximal leg portion with respect to said distal leg portion.

14. A dynamic external fixator for maintaining a predetermined relationship between a wrist, hand and arm including an ulna, comprising:
 (a) a proximal leg portion including first means for retaining at least one bone fixation pin therein;
 (b) a distal leg portion including second means for retaining at least one hand bone fixation pin therein;
 (c) joint means connecting said proximal leg portion to said distal leg portion and facilitating relative movement therebetween; and
 (d) selectively positionable control means cooperating with said joint means, during a period of patient treatment, for selectively restricting the range of motion through which said joint means is free to move, said control means being infinitely adjustable from a position permitting unrestrained movement of said joint means to another position which substantially prevents movement of said joint means thereby adjustably permitting ulnar deviation of said hand during flexation of said wrist.

15. A dynamic external fixator for maintaining a predetermined relationship between bones associated with a joint comprising:
 (a) a proximal leg portion including first means for retaining at least one bone fixation pin therein;
 (b) a distal leg portion including second means for retaining at least one bone fixation pin therein;
 (c) joint means connecting said proximal leg portion to said distal leg portion and facilitating relative movement therebetween; and
 (d) means for permitting adjustment of the effective length of one of said leg portions during flexation of said joint whereby said means for permitting adjustment of the effective length acts to constrain the motion of said at least one bone fixation pin associated with said distal leg portion to a direction along a longitudinal axis of said distal leg portion during flexation of said joint means.

16. The invention of claim 15, wherein said one of said leg portions comprises said distal leg portion.

17. A method of treating a Colles fracture of the distal radius of an arm comprising the steps of:
 (a) forming at least one hole in the radius of said arm and at least one hole in a bone of an associated hand;
 (b) fixedly placing a bone fixation pin first end in each said hole;

(c) fixedly attaching a second end of the bone fixation pin associated with each said radius hole to a proximal leg of a dynamic external fixator;

(d) fixedly attaching a second end of the bone fixation pin associated with each said hand bone hole to a distal leg of said dynamic external fixator;

(e) providing said dynamic external fixator with joint means connecting said proximal leg with said distal leg;

(f) orienting said dynamic external fixator so as to align said joint means thereof with the center of rotation of the wrist associated with said hand and arm in one plane thereof; and (g) selectively restricting, with control means, the range of motion of said joint means during a period of patient treatment, said control means being infinitely adjustable from a position permitting unrestrained joint means movement to another position which substantially prevents movement of said joint means.

18. A dynamic external fixator comprising:
(a) a proximal leg portion including first means for retaining at least one bone fixation pin therein, said first means comprising a first hole for receiving therethrough a bone fixation pin, and a second hole intersecting said first hole and threadably receiving a locking screw which frictionally engages said bone fixation pin to thereby retain said bone fixation pin in a predetermined orientation;

(b) a distal leg portion including second means for retaining at least one bone fixation pin therein, said distal leg portion including adjusting means for allowing controllable elongation and contraction thereof, said second means forming a part of said adjusting means;

(c) universal joint means connecting said proximal leg portion to said distal leg portion and facilitating substantially universal movement therebetween; and (d) selectively positionable control means cooperating with said universal joint means, during a period of patient treatment for selectively restricting the range of motion through which said universal joint means is free to move, said control means being infinitely adjustable from a position permitting unrestrained movement of said universal joint means to another position which substantially prevents movement of said universal joint means and thereby adjustably controlling the freedom of motion of said proximal leg portion with respect to said distal leg portion.

19. A dynamic external fixator comprising:
(a) a proximal leg portion including first means for retaining at least one bone fixation pin therein, (b) a distal leg portion including second means for retaining at least one bone fixation pin therein, said distal leg portion including adjusting means for allowing controllable elongation and contraction thereof, said second means forming a part of said adjusting means;

(c) universal joint means connecting said proximal leg portion to said distal leg portion and facilitating substantial universal movement therebetween;

(d) selectively positionable control means cooperating with said universal joint means, during a period of patient treatment, for selectively restricting the range of motion through which the universal joint means is free to move, said control means being infinitely adjustable from a position permitting unrestrained movement of said universal joint means to another position which substantially prevents movement of said universal joint means and thereby adjustably controlling the freedom of motion of said proximal leg portion with respect to said distal leg portion;

(e) said selectively positionable control means comprising:
(1) a first sleeve fixedly mounted on one of said proximal or distal leg portions;
(2) a second sleeve adjustably mounted on said universal joint means; and
(3) said first sleeve including a first face facing a second face on said second sleeve, whereby when said first face abuts said second face, said universal joint means is substantially frozen in a fixed position and when said second sleeve is moved away from said first sleeve to thereby define a spacing between said first face and second face, said universal joint means allows movement between said proximal and distal leg portions to an extent defined by said spacing;

(f) and further wherein said first sleeve has a longitudinal axis coinciding with a longitudinal axis of said one of said proximal or distal leg portions, said first face comprising a flat face in a plane at an obtuse angle to said longitudinal axis of said one of said proximal or distal leg portions being connected to said universal joint means and having a longitudinal axis aligned with said first sleeve longitudinal axis, whereby when said first face abuts said second face, said proximal leg portion is oriented at an obtuse angle to said distal leg portion.

20. A dynamic external fixator comprising:
(a) a proximal leg portion including first means for retaining at least one bone fixation pin therein;

(b) a distal leg portion including second means for retaining at least one bone fixation pin therein said distal leg portion including adjusting means for allowing controllable elongation and contraction thereof, said second means forming a part of said adjusting means;

(c) universal joint means connecting said proximal leg portion to said distal leg portion and facilitating substantially universal movement therebetween; and (d) selectively positionable control means cooperating with said universal joint means, during a period of patent treatment, for selectively restricting the range of motion through which said universal joint means is free to move, said control means being infinitely adjustable from a position permitting unrestrained movement of said universal joint means to another position which substantially prevents movement of said universal joint means and thereby adjustably controlling the freedom of motion of said proximal leg portion with respect to said distal leg portion.

* * * * *

UNITED STATES PATENT AND TRADEMARK OFFICE
CERTIFICATE OF CORRECTION

PATENT NO. : 4,628,919
DATED : December 16, 1986
INVENTOR(S) : TERRY A. CLYBURN

It is certified that error appears in the above-identified patent and that said Letters Patent is hereby corrected as shown below:

Claim 1, line 20, (column 8, line 42),
    delete "patent", insert --patient--.

Claim 20, line 16, (column 12, line 55),
    delete "patent", insert --patient--.

Signed and Sealed this

Seventeenth Day of March, 1987

*Attest:*

DONALD J. QUIGG

*Attesting Officer*          *Commissioner of Patents and Trademarks*